(12) United States Patent

Huang et al.

(10) Patent No.: US 7,164,014 B2
(45) Date of Patent: Jan. 16, 2007

(54) PROTECTED LINKER COMPOUNDS

(75) Inventors: Tai-Nang Huang, Lexington, MA (US); Ming Shen, Guilford, CT (US)

(73) Assignee: Linden Technologies, Inc., Woburn, MA (US)

( * ) Notice: Subject to any disclaimer, the term of this patent is extended or adjusted under 35 U.S.C. 154(b) by 948 days.

(21) Appl. No.: 10/256,510

(22) Filed: Sep. 27, 2002

(65) Prior Publication Data

US 2003/0105056 A1 Jun. 5, 2003

Related U.S. Application Data

(60) Provisional application No. 60/325,897, filed on Sep. 27, 2001.

(51) Int. Cl.
*C07H 19/04* (2006.01)
*C07H 21/00* (2006.01)
*C07F 9/02* (2006.01)

(52) U.S. Cl. .................... 536/26.1; 536/25.4; 544/243; 544/244; 548/414

(58) Field of Classification Search ............... 536/26.1, 536/25.4; 544/243, 244; 548/414
See application file for complete search history.

(56) References Cited

U.S. PATENT DOCUMENTS 5,039,819 A    8/1991   Kieczykowski

OTHER PUBLICATIONS

Aronov and Gelb, "Phthalimide Resin Reagent for Efficient Mitsunobu Amino-Dehydroxylation", *Tetrahedron Letters* 39:4947-4950 (1998).
Bressi et al., "Adenosine Analogues as Selective Inhibitors of Glyceraldehyde-3-phosphate Dehydrogenase of *Trypanosomatidae* via Structure-Based Drug Design", *J. Med. Chem.* 44:2080-2093 (2001).

*Primary Examiner*—Elli Peselev
*Assistant Examiner*—Howard V. Owens
(74) *Attorney, Agent, or Firm*—Fish & Richardson P.C.

(57) ABSTRACT

The invention features linker molecules that have at one terminus a amino-protecting group and at the other terminus a phosphorous activating group, typically phosphoramidite. The linker molecules can be used, for example, to produce amino-modified linkers that space an oligonucleotide from a solid support. The invention also features an amino-protected nucleotide that includes an activated phosphorous group such as a phosphoramidite for the production of a 5' amino-modified oligonucleotide. The invention further provides a phthalimido-modified support that can be used to synthesize a polynucleotide that includes an amino group at the 3' terminus.

23 Claims, 6 Drawing Sheets

PROTECTED LINKER COMPOUNDS

CROSS REFERENCE TO RELATED APPLICATIONS

Pursuant to 35 USC §119(e), this application claims the benefit of prior U.S. provisional application No. 60/325,897 filed Sep. 27, 2001.

BACKGROUND

The availability of nucleic acid sequence information has enabled large-scale and detailed analysis of cellular and molecular processes. Among the many applications for such analyses, it is convenient to attach a nucleic acid to a solid support.

Arrays of nucleic acids are used to locate different nucleic acid sequences in an addressable format. The arrays have applications in analyzing nucleic acids in a sample, analyzing genetic polymorphisms, nucleic acid sequencing, research, and diagnostics. By design, the arrays are suited for high-throughput analysis.

For example, nucleic acid arrays can be used for the for large-scale gene expression studies (see, e.g., U.S. Pat. No. 5,889,165). These studies determine the levels of expression of a large proportion of genes present in the genome. Generally, the arrays can be used in a variety of hybridization assays, but also in enzymatic reactions such as nucleic acid extension reactions. For example, nucleic acid arrays can be used for solid phase PCR (see, e.g., WO 01/48242 A2), sequencing by hybridization (see, e.g., U.S. Pat. No. 5,695,940), and single-base extension reactions (see, e.g., U.S. Pat. No. 6,004,774).

A variety of chemistries can be used to link a nucleic acid to a solid support. In one method, the nucleic acid is modified with a sulfhydryl group and reacted with a mercaptosilane coated solid phase. See, e.g., U.S. Pat. No. 6,030,782. U.S. Pat. No. 6,169,194 describes high-density immobilization of sulfhydryl modified oligonucleotides using a permanent thioether bond. In still another method, a covalent bond between a modified oligonucleotide and a solid phase surface is formed by a condensation reaction with a water-soluble carbodiimide as described by Rasmussen et al. (1991) *Anal. Biochem.* 198:138–142. Markos et al. (1992) *Nucl. Acids Res.* 20:1679–1684 describes a flexible linker with a primary hydroxyl group that is coupled to the solid phase by a glycidoxypropyl silane. U.S. Pat. No. 6,171,797 describes a cycloaddition reaction between a diene with a dienophile to couple a nucleotide to a substrate.

Another method of attaching nucleic acids to solid supports uses amine-modified nucleic acids. The amine group is used as a functional group that reacts with a solid support. For example, the solid support can be an aldehyde coated glass substrate (see, e.g., U.S. Pat. No. 6,030,782). The amine linkage is robust and can be used to orient the nucleic acid with respect the solid support by selective introduction of the amine group.

One method of synthesizing amino-modified nucleic acids uses β-cyanoethyl phosphoramidites that are attached to the 5' terminus of an oligonucleotide.

SUMMARY

The invention provides efficient, versatile and economical approaches for synthesizing amine linked nucleic acids.

One aspect of this invention relates to a compound of formula (I):

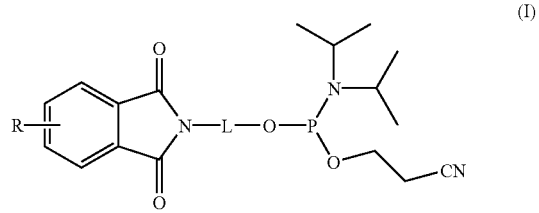

Referring to formula (I), R is hydrogen, $C_{1-6}$ alkyl, $C_{1-6}$ alkoxyl, or a halogen; and L is a bond, a nucleotide residue, a nucleotide oligomer, aryl, heteroaryl, $C_{1-14}$ cycloalkyl, $C_{1-12}$ heterocycloalkyl, S, NH, or $(R_1-(O)_m)_n-R_1$, in which $R_1$ is $C_{1-4}$ alkylene, $C_{1-4}$ alkenylene, or $C_{1-4}$ alkynylene, m is 1 or 0, and n is 1 to 12. The nucleotide oligomer can be a trinucleotide. Examples of these compounds include those in which $R_1$ is $CH_2CH_2$ or n is 1–4. In one embodiment, L includes both a nucleotide oligomer and $(R_1-(O)_m)_n-R_1$.

Another aspect of this invention relates to a compound of formula (II):

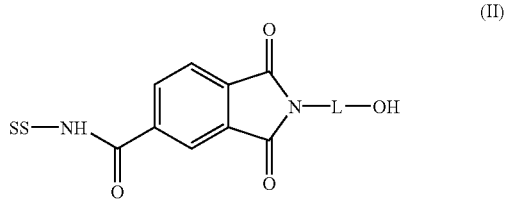

Referring to formula (II), R is hydrogen, $C_{1-6}$ alkyl, $C_{1-6}$ alkoxyl, or a halogen; and L is a bond, a nucleotide residue, aryl, heteroaryl, $C_{1-14}$ cycloalkyl, $C_{1-12}$ heterocycloalkyl, S, NH, or $(R_1-(O)_m)_n-R_1$, in which $R_1$ is $C_{1-4}$ alkylene, $C_{1-4}$ alkenylene, or $C_{1-4}$ alkynylene, m is 1 or 0, n is 1 to 12, and SS is a solid support. Examples of these compounds include those in which $R_1$ is $CH_2CH_2$ or n is 1–4. The solid support can be, for example, a bead (e.g., controlled pore glass) or a planar array (e.g., a glass slide).

In a related aspect, the invention features the following compound:

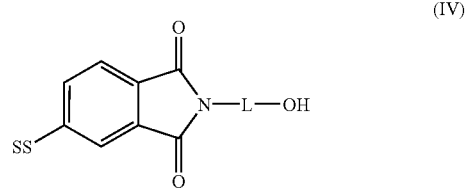

Referring to formula (IV), R is hydrogen, $C_{1-6}$ alkyl, $C_{1-6}$ alkoxyl, or a halogen; and L is a bond, a nucleotide residue, aryl, heteroaryl, $C_{1-14}$ cycloalkyl, $C_{1-12}$ heterocycloalkyl, S, NH, or $(R_1-(O)_m)_n-R_1$, in which $R_1$ is $C_{1-4}$ alkylene, $C_{1-4}$ alkenylene, or $C_{1-4}$ alkynylene, m is 1 or 0, n is 1 to 12, and SS is a solid support. Examples of these compounds include those in which $R_1$ is $CH_2CH_2$ or n is 1–4. The solid support can be, for example, a bead (e.g., controlled pore glass) or a planar array (e.g., a glass slide).

Still another aspect of this invention relates to a compound of formula (III):

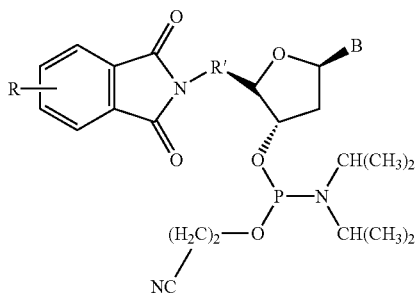

Referring to formula (III), R is hydrogen, $C_{1-6}$ alkyl, $C_{1-6}$ alkoxyl, or a halogen; R' is $C_{1-12}$ alkylene, $C_{1-12}$ alkenylene, or $C_{1-12}$ alkynylene; and B is a nucleotide base. Examples of these compounds include those in which R is H, R' is $CH_2$, or B is adenine, guanine, cytidine, uridine, and thymidine.

The invention also relates to a method of preparing a polynucleotide. The method includes the steps of providing a compound of formula (II) or (IV); coupling a first nucleotide to the terminal hydroxyl group of the compound of formula (II) or (IV) to obtain a nucleotide-containing compound; and treating the nucleotide-containing compound with a strong base to release a compound that contains the first nucleotide and a 3' amino group. The strong base can be ammonia.

The method can further include, before the treating, sequentially coupling additional nucleotides or additional nucleotide oligomers to the first nucleotide or the first nucleotide oligomer to form an extended polynucleotide attached to the support. In this case, the strong base releases the extended polynucleotide with a 3' amino group. Optionally, the released extended polynucleotide is separated from the 3' amino group by a linker.

Also within the scope of this invention is a method of preparing a 5' amino labeled nucleotide. The method includes the steps of sequentially coupling nucleotides (e.g., mononucleotides and oligonucleotides such as a trinucleotide) to a solid support to obtain a precursor oligonucleotide; coupling a compound of formula (I) or (III) to the terminus of the precursor oligonucleotide thereby forming a terminated oligonucleotide; and treating the terminated oligonucleotide with a strong base to release the terminated oligonucleotide and the modifying group (e.g., the phthalimide group) to form a 5' amino labeled oligonucleotide. The 5' amino group can be spaced from the oligonucleotide by a linker.

The method can further include coupling the 5' amino labeled oligonucleotide to a substrate, e.g., a solid support such as a planar array or to a bead such as controlled pore glass.

In another aspect, the invention features a method of providing a nucleic acid array. The method includes synthesizing a plurality of 3' or 5' amino labeled oligonucleotides using a method described herein, and disposing each oligonucleotide of the plurality on a unique address of a substrate (e.g., a planar substrate). The substrate is reactive with amines such that the amino groups of the oligonucleotides are covalently linked to the substrate. In one embodiment, the substrate has a reactive aldehyde surface. In another embodiment, the oligonucleotides also include a linker, e.g., a linker that spaces the oligonucleotides from the substrate when coupled to the substrate.

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. The term "alkoxyl" refers to an —O-alkyl radical. The term "alkylene" refers to a divalent alkyl (i.e., —R—). Similarly, the terms "alkenylene" and "alkynylene" refer to divalent alkenyl and alkynyl, respectively.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "heteroaryl" refers to an aromatic 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "nucleotide" refers to a nucleotide monomer. "Polynucleotides" and "nucleotide oligomers" refer to a nucleotide polymer that includes at least two nucleotides. A "nucleotide base" is the base that is attached to the ribose sugar of a nucleotide. The term includes natural and unnatural bases that can pair (albeit with lower energy) natural bases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The methods and compounds of the invention provide convenient and efficient means for the high-throughput and large-scale production of modified polynucleotides at relatively low cost. Such polynucleotides can be used, among other things, for the preparation of microarrays and genomic analyses. Genomics analysis and nucleic acid microarrays have increased the need for large-scale modified oligonucleotides.

DETAILED DESCRIPTION

The invention is based, in part, on the discovery that phthalimide can be used to protect an amine group on linkers and nucleic acid. The phthalimide moiety is conveniently released by ammonia. Further, the phthalimide moiety can be used to modify a compound that is activated with a phosphorous activating group for coupling to a nucleotide or nucleic acid.

The inventive concepts have lead to the development of a number of versatile compounds and methods.

Protected Linker Compounds

In one aspect, the invention provides linker molecules that have at one terminus a amino-protecting group and at the other terminus a phosphorous activating group, typically phosphoramidite. Generally, any linking compound can be located between the two termini. These linker molecules can be represented as follows:

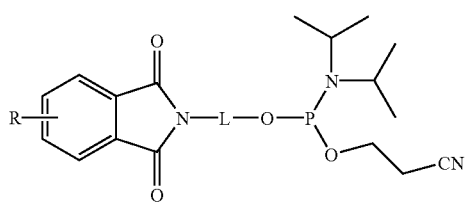

(I)

Where R is hydrogen or optionally alkyl, alkoxyl or halogens; and L is a linking group. For example, L can be polyethylene glycol, —(CH$_2$CH$_2$O)$_n$—, where n is 1 to 8. In another example, L is a linking group containing polymethylene, —(CH$_2$)$_n$—, where n is 2 to 18. These linking groups provide a convenient extended structure that can be used to space moieties that are later attached to either terminus. More generally, L can be any useful linking compound. For example, L can be a nucleotide monomer as described in section "Amino Protected Nucleotides," below.

The activated phosphorous group is depicted as a phosphoramidite above. However, the activated phosphorous group can be any reactive derivative having a high coupling efficiency, examples of which include, but are not limited to, phosphate-triesters, phosphoramidite, or the like.

Figure 1:
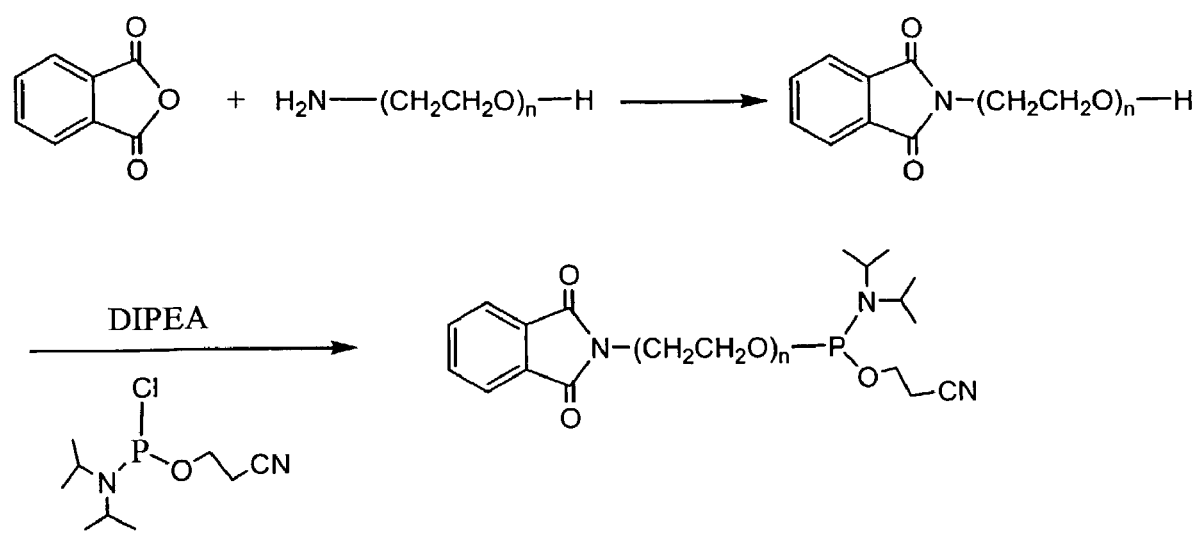
FIG. 1 is a schematic of an exemplary method for preparing a polyethylene glycol linker that is protected on one terminus by phthalimide and activated on the other by phosphoramidite.
Figure 2:
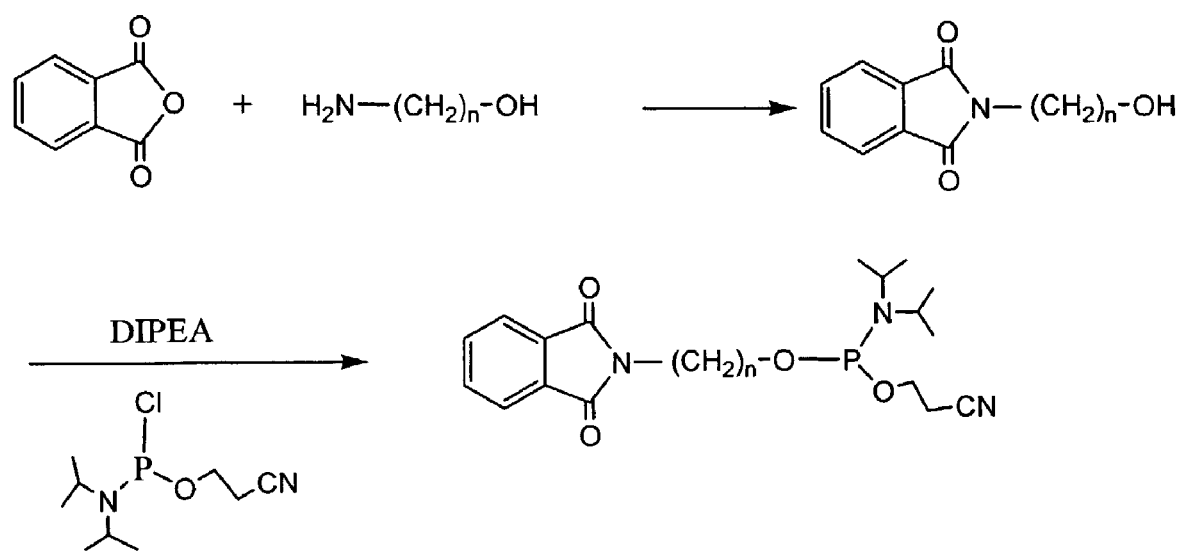
FIG. 2 is a schematic of an exemplary method for preparing a polymethylene linker that is protected on one terminus by phthalimide and activated on the other by phosphoramidite.

Referring to FIGS. 1 and 2, the amine-protected linker compound can be synthesized from a linker compound that has an amino group at one terminus and a hydroxyl group at the other. The linker compound is first treated with phthalic anhydride to form phthalimide. The terminal hydroxyl group of the linker is activated with phosphoramidite. In an alternative embodiment, the linker compound does not include an amino group. Rather the amino group is introduced directly with phthalimide or di-tert-butyl iminodicarbonate using the Mitsunobu reaction (see, e.g., Gelb et. al. (2001) *J. Medicinal Chemistry* 44:2080–2093 and Subramanyam (2000) *Tetrahedron letters* 41:6537–6540).

Attachment Method for Amino Protected Linkers

The amine-protected and phosphorous-activated linker compound has a variety of uses. One exemplary use is the synthesis of a compound that includes a polynucleotide, a linker, and an amino group. The amino group is at a terminus of the linker and can be used to attach the compound to a substrate, e.g., a solid support.

Oligonucleotides are typically synthesized on a solid support in the 3' to 5' direction using cycles of nucleotide addition. The terminal nucleotide of a oligonucleotide being synthesized has a free hydroxyl at the C-5'. The support is contacted with a modified nucleotide that includes the base which is desired at the position after the current terminal position. The modified nucleotide has a phosphoramidite at the C-3' and a protecting group, such as a trityl protecting group, at the C-5' position.

The phosphorous activating group, typically phosphoramidite, reacts with a hydroxyl group. The reaction can be performed in an acetonitrile solution in which tetrazole or another activator compound, such as 5-(p-nitrophenyl)-1H-tetrazole, 5-ethylthio-1H-tetrazole, 4,5-dichloroimidazole, benzimidazolium triflate, or 4,5 dicyanoimidazole. The concentration of the activator compound can be between 0.1M and 1.0M, e.g., 0.2M to 0.8M or 0.2M to 0.6M.

After the modified nucleotide is attached and excess reagents removed, the protecting group is removed, yielding a C-5' hydroxyl available for the next cycle of addition. It is also contemplated that oligonucleotide synthesis can include addition of polynucleotides such as di- and tri-nucleotides, e.g., as described in U.S. Pat. No. 5,869,644.

Figure 3:
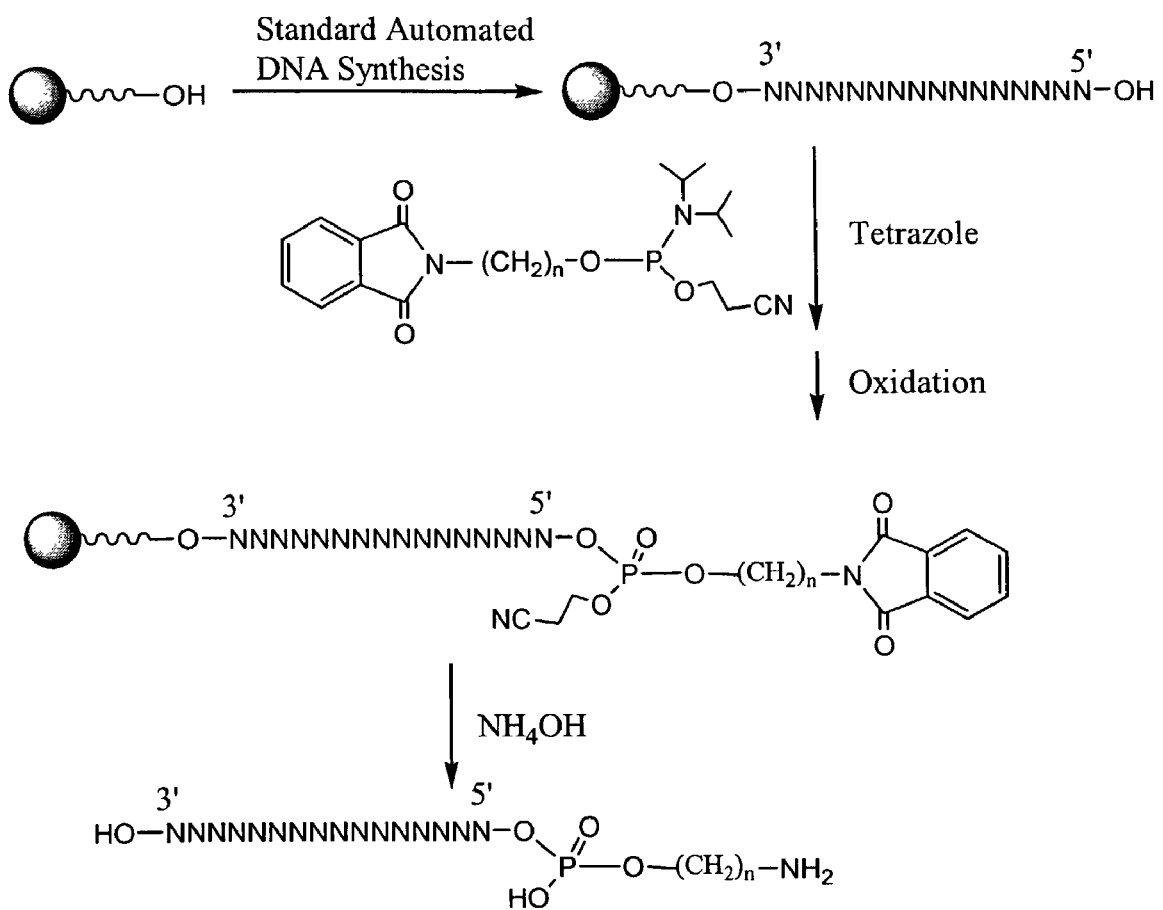
FIG. 3 is a schematic of an exemplary method for preparing a 5'-amine linker modified oligonucleotide using the phthalimide phosphoramidite polymethylene linker.

Advantageously, the amine-protected and phosphorous-activated linker compounds described herein can be added to an oligonucleotide formed by this synthetic process in an addition step that is analogous to the nucleotide addition steps. Referring to FIG. 3, a phthalimide protected and phosphoramidite activated polymethylene linker is attached to the oligonucleotide after the completion of its synthesis. Upon addition of the activator compound, in this case tetrazole, the polymethylene linker is attached to the C-5' of the oligonucleotide. The support is then oxidized.

Subsequently, ammonia is added to cleave the oligonucleotide-linker compound from the solid support. It is a particular advantage of the invention that the ammonia treatment also removes the phthalimide group thereby producing an oligonucleotide with a C-5' linker having a terminal amino group.

The oligonucleotide-linker compound can be attached to a solid support. For example, the oligonucleotide-linker compound can be spotted onto a planar substrate that is reactive with amino groups, e.g., an aldehyde slide. Because the amino group is at the terminus of the linker, the oligonucleotide is oriented relative to the solid support. The C-3' is free and can be used in a nucleic acid polymerization reaction, e.g., single-base extension (see, e.g., U.S. Pat. No. 6,004,774), or a solid phase nucleic acid amplification, such as solid-phase PCR (see, e.g., PCT WO 01/48242)). The attached oligonucleotide can also be used as a probe in a hybridization reaction. In still another example, the oligonucleotide includes a nucleic acid aptamer which has catalytic activity or a binding activity, e.g., for a polypeptide.

Amino Protected Nucleotides

The invention also features an amino-protected nucleotide that includes an activated phosphorous group such as a phosphoramidite. The amino-protected group is located at the 5' end and the phosphoramidite at the 3' end. The amino-protected nucleotide can be represented by formula (III):

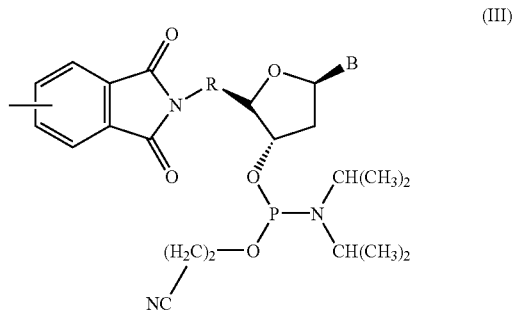

Figure 5:
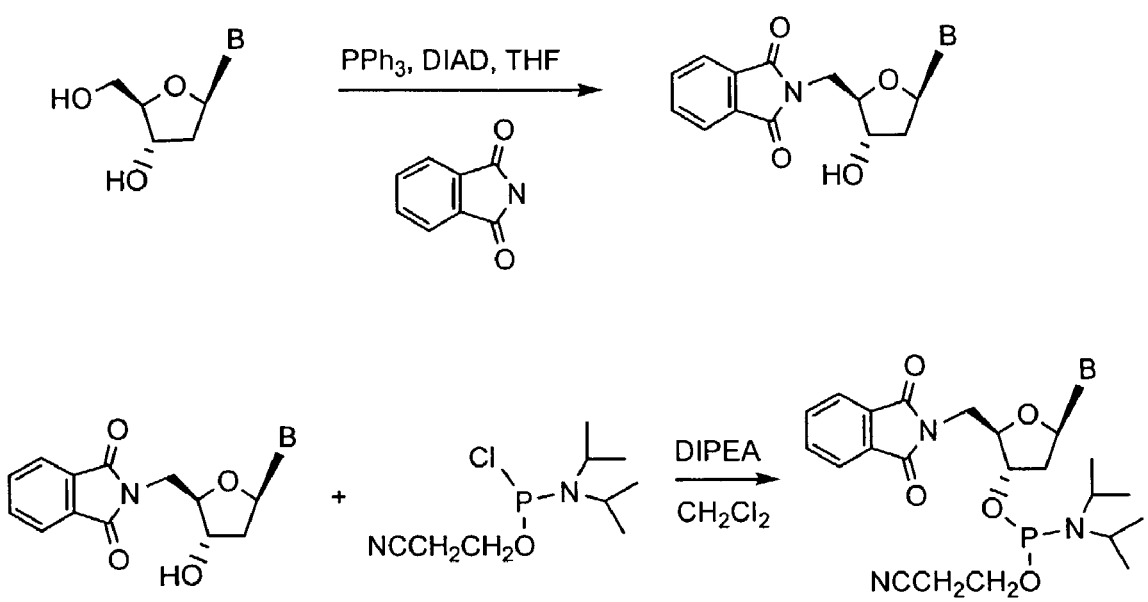
FIG. 5 is a schematic of an exemplary method for preparing a 5'-amine modified nucleotide monomer where phosphoramidite is used to activate the 3' hydroxyl group.

One method for preparing such a compound is depicted in FIG. 5. A nucleotide is reacted with phthalimide in $PPh_3$, DIAD, and THF. Then the phthalimide-modified nucleotide is activated with phosphoramidite by reaction with diisopropylamino(cyanoethoxyl)chlorophosphine in chloroform and DIPEA.

The invention also provides dinucleotide, trinucleotides, and oligonucleotides that are similarly amino-protected at one terminus and activated at another terminus.

Construction of Amino-Modified Oligonucleotides

Figure 6:
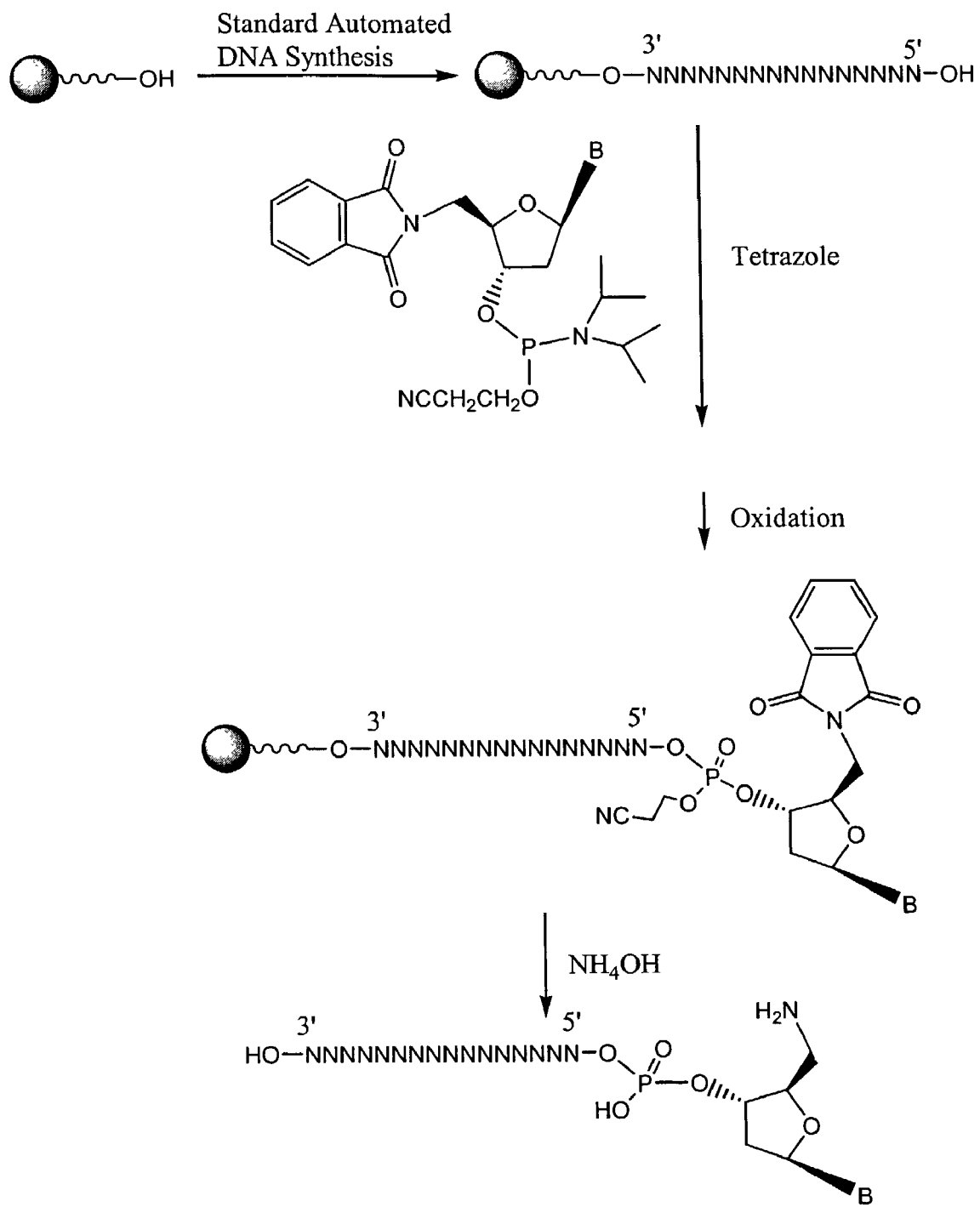
FIG. 6 is a schematic of an exemplary method using a 5'-amine modified nucleotide monomer as a linker to attach at the 5' terminus of an oligonucleotide to facilitate immobilization on solid support.

Referring to the example in FIG. 6, the amino-protected nucleotide (or oligonucleotide) can be used to terminate the chemical synthesis of an oligonucleotide, e.g., an oligonucleotide attached to a support as is typical in conventional automated oligonucleotide synthesis. The last nucleotide to be added is phthalimide-protected at the C-5' and phosphoramidite activated at the C-3'. Upon addition of tetrazole, the nucleotide is attached to the C-5' of the oligonucleotide. The support is then oxidized.

Subsequently, ammonia is added to cleave the oligonucleotide-linker compound from the solid support. Again, the ammonia treatment concurrently removes the phthalimide group thereby producing an oligonucleotide with a C-5' terminal amino group.

The amino-modified oligonucleotide can be coupled to a substrate that is reactive with amines. Alternatively, the amino-modified oligonucleotide can be used in a variety of procedures prior to coupling. For example, an oligonucleotide bearing a 5' amino group can be used as a primer for nucleic acid synthesis, e.g., DNA polymerization. The resulting strand formed from extending the primer includes the amino group. The extended strand can now be reacted with a solid support that is reactive with amines.

The amino-modified oligonucleotide can also be used for other implementations. For example, the amino group can be reacted with an amine reactive fluorophore (e.g., Alexa Fluor 488 dye from Molecular Probes, Eugene Oreg.) in order to fluorescently label the oligonucleotide. Fluorescently labeled oligonucleotides are useful for fluorescence resonance energy transfer (FRET) analyses and fluorescence polarization (FP) analyses.

In still another implementation, the phthalimide-protected oligonucleotide is removed from the support, e.g., using an enzyme, such that the phthalimide group is retained. The phthalimide-protected oligonucleotide is used in any of a variety of methods, then treated with a strong base (e.g., ammonia) to remove the phthalimide group prior to coupling to a solid support a solid support that is reactive with amines. The use of ammonia (as compared to conventional agents such as hydrazine) is unexpectedly efficacious as it can used to concurrently remove an oligonucleotide from a support bed as is typically done during the final stage of oligonucleotide synthesis.

Ammonia-Sensitive Supports

The invention also features a solid support that is depicted as follows:

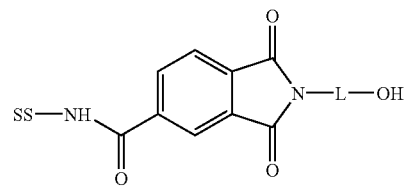

L can be any convenient linking group. For example, the linking group can include polyethylene glycol ($(CH_2CH_2O)_n$—, e.g., where n is 1 to 8) and/or polymethylene, ($(CH_2)_n$—, e.g., where n is 2 to 18). In some embodiments, the L group is a bond. The solid support can be, for example, a polymer bead, controlled pore glass bead, a planar polymer sheet or a glass slide. The solid support can be used to synthesize a 3' amino modified polynucleotide, e.g., as described below. Compound IV (see above) can also be used.

Synthesis of 3' Amino-Modified Polynucleotides

Figure 4:
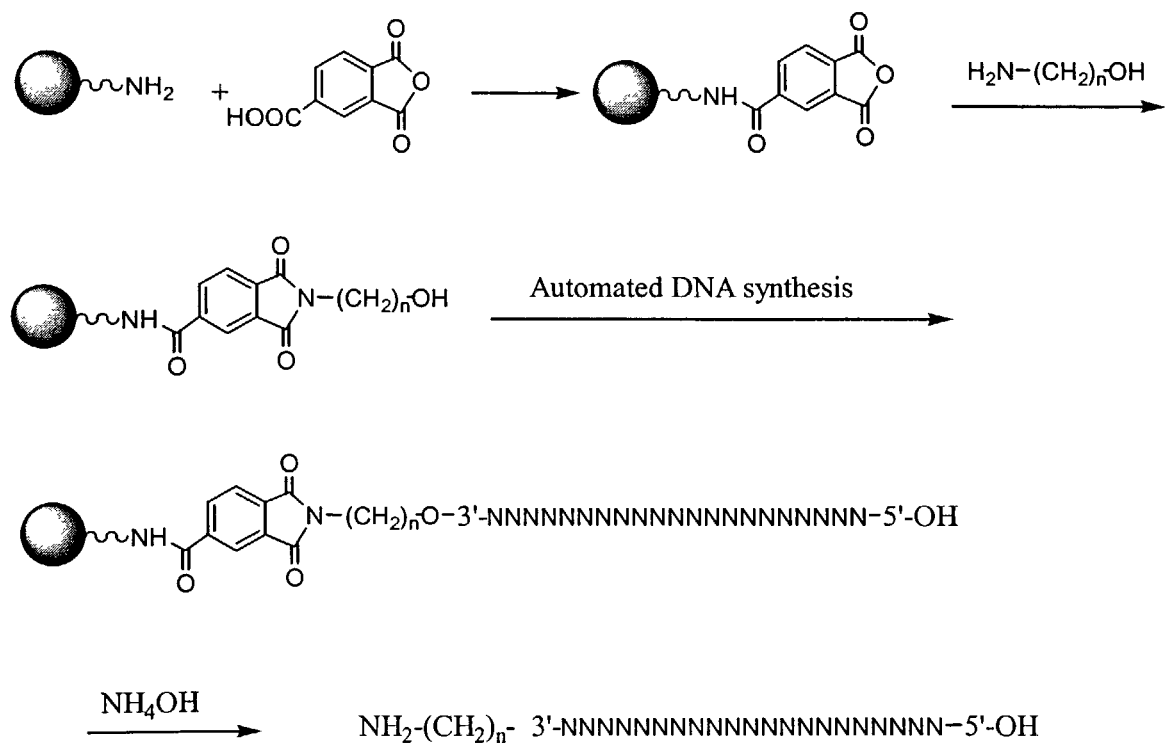
FIG. 4 is a schematic of an exemplary method for preparing a 3' amine linker modified oligonucleotide using the phthalimide polyethylene glycol coated solid support.

The phthalimido-modified support can be used to synthesize a polynucleotide that includes an amino group at the 3' terminus. Referring to the example in FIG. 4, a linker group that includes an amino terminus is attached to the phthalimido-modified support. Then standard oligonucleotide synthesis procedures, e.g., as described above, are used to couple nucleotides or polynucleotides to the other terminus of the attached linker. After sequential couplings, the oligonucleotide and linker group can be readily removed from the support by treatment with a strong base such as aqueous ammonia. The treatment yields a 3' amino-modified polynucleotide in which the 3' amino group is spaced from the polynucleotide by the linker region (e.g., a polyethylene glycol or polymethylene linker).

Amino-Reactive Solid Supports

One type of substrate that can be used to couple amino-modified nucleic acids is an aldehyde slide (see, e.g., Ruuska, ArrayIt™ Super Microarray Substrates Handbook, pp. 6–7, 1999, TeleChem International, Inc). The amino groups of the modified nucleic acid attacks the aldehyde functional group on the slide forming an unstable intermediate to generate a Schiff base by dehydration. After the Schiff base is formed, the remaining unreacted aldehyde groups and the Schiff base C=N bond are reduced by treatment with sodium borohydride.

All cited references, patents, and patent applications are incorporated by reference in their entirety. The following examples are merely illustrative of particular aspects of the invention described herein. As would be apparent to the skilled artisan, various changes, modifications and applications are also within the scope of the invention.

EXAMPLES

Conversion of $N^6$-Benzoyl-2'-deoxyadenosine to 5'-Phthalimido-$N^6$-benzoyl-2',5'-dideoxyadenosine-3'-O-(2-cyanoethyl-N,N-diisopropylphosphoramidite

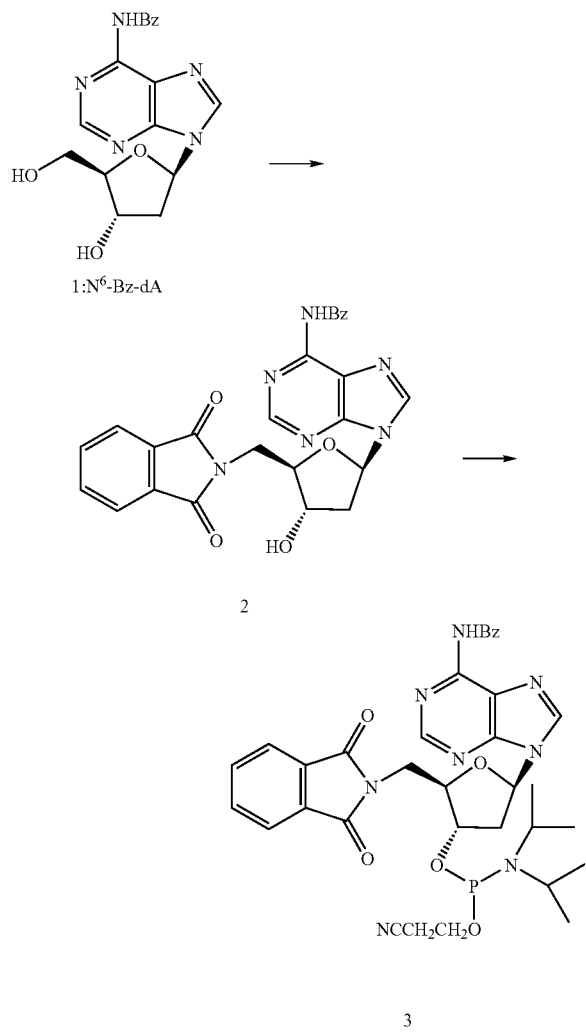

Synthesis of 5'-phthalimido-$N^6$-benzoyl-2',5'-dideoxyadenosine, 2.

To a stirred solution of 13.11 g (50 mmol) Ph₃P, 6.99 g (47.5 mmol) phthalimide and 17.77 g (50 mmol) $N^6$-benzoyl-2'-deoxyadenosine in 400 mL dry THF was added 9.84 mL (50 mmol) of diisopropyl azodicarboxylate under a nitrogen atmosphere. The resulting mixture was stirred for 2 h in an ice water bath and then 4 h at room temperature. After most of the THF was evaporated under reduced pressure, the oily residue was added 100 ml of dichloromethane. The precipitate, which was formed after the addition of dichloromethane, was filtered and washed with small amounts of THF/dichloromethane mixture (1:1). The filtrate was concentrated and purified with a silica gel column chromatography (dichloromethane/THF=2:1 then dichloromethane/methanol=19:1) to give 7.1 g of compound 2.

Synthesis of 5'-phthalimido-$N^6$-benzoyl-2',5'-dideoxyadenosine-3'-O-(2-cyanoethyl-N,N-diisopropylphosphoramidite, 3.

To a solution of 4.22 g (8.71 mmol) phthalimide derivative 2 and 3.94 g (13.07 mmol) N,N,N',N'-tetraisopropyl phosphorodiamidite in 75 mL dry THF at 40° C. was added 0.46 g (6.56 mmol) tetrazole. The resulting mixture was stirred at 40° C. for 10 h. After the THF was evaporated under reduced pressure, the residue was dissolved in 75 mL of dichloromethane, which was then washed with water (30 mL×2), saturated sodium bicarbonate (20 mL), and then water again (20 mL×1). The organic phase was concentrated to about 20 mL, which was then passed through a short silica gel column. The eluted solution was concentrated to about 20 mL and then 100 mL of hexanes was added to precipitate the desired product. After decanting of the supernatant, the oily residue was dried overnight with an oil vacuum pump to give 5.75 g of final product 3.

Synthesis of Mobile Phase and Solid Phase Linkers Terminated with a Phthalimido Group Synthesis of 5'-phthalimido-$N^6$-benzoyl-2'-deoxyadenosine-3'-O-(2-cyanoethyl-N,N-diisopropylphosphoramidite.

13.11 g (50 mmol) triphenylphosphine, 6.99 g (47.5 mmol) phthalimide and 17.77 g (50 mmol) $N^6$-benzoyl-2'-deoxyadenosine were stirred in 400 mL dry THF, and added 9.84 mL (50 mmol) of diisopropyl azodicarboxylate under a nitrogen atmosphere. After stirring in an ice-water bath for 2 h and at the ambient temperature for 4 h, the reaction mixture was concentrated and the residue was added 100 mL dichloromethane. The precipitates thus formed were removed by filtration and the filtrate was concentrated and flashed through a silica gel column with 2:1 dichloromethane-THF and 19:1 dichloromethane-methanol to give 7.1 g of 5'-phthalimido-$N^6$-benzoyl-2'-deoxyadenosine.

4.22 g (8.71 mmol) 5'-phthalimido-$N^6$-benzoyl-2'-deoxyadenosine and 3.94 g (13.1 mmol) 2-cyanoethyl N,N,N',N'-tetraisopropyl phosphorodiamidite were stirred in 75 mL dry THF at 40° C., and added 0.46 g (6.56 mmol) tetrazole. After stirring at 40° C. for 10 h, the reaction mixture was stripped and the residue was dissolved in 75 mL dichloromethane. The dichloromethane solution was washed with 2×20 mL water, 20 mL saturated sodium bicarbonate, and 20 mL water, and concentrated to about 20 mL The concentrated solution was then flashed through a short silica gel column with dichloromethane. The desired fractions were collected, combined and concentrated to about 20 m, and the desired product was oiled out by the addition of hexane. After decanting the supernatant, the oily residue was dried under high vacuum overnight to give 5.75 g of product 1. $^1$H NMR(CDCl₃): 9.1 (s, 1H), 8.65 (s, 1H), 8.29 (d, 1H), 8.02 (d, 2H), 7.82 (m, 2H), 7.71 (m, 2H), 7.61 (t, 1H), 7.53 (3, 2H), 6.4 (m, 1H), 4.8 (m, 1H), 4.5 (m, 1H), 3.5–4.3 (m, 17H), 3.04 (m, 1H), 2.6–2.8 (m, 4H), 1.27 (dd, 4H), 1.17 (dd, 8H).

Synthesis of 2-(phthalimido)ethyl-2-cyanoethyl-N, N-diisopropylphosphoramidite.

4.2 mL 2-Cyanoethyl diisopropylchlorophosphoramidite were added dropwise to a stirred mixture of 3.0 g N-(2-hydroxyethyl)phthalimide and 3.30 mL diisopropylethylamine in 30 mL dichloromethane under a nitrogen atmosphere. After stirring at the ambient temperature for about three hr., the reaction mixture was stripped to give a yellow oily residue. This oily residue was flashed through a silica gel column with 1:4 and 1:3 ethyl acetate-hexane, and the desired fractions were collected, combined, stripped and dried under high vacuum. 3.8 g of 2 were obtained. $^1$H NMR(CDCl$_3$): 7.85 (dd, 2H), 7.72 (dd, 2H), 3.95–3.70 (m, 6H), 3.51 (m, 2H), 2.58 (t, 2H), 1.08–1.12 (dd, 12H).

Synthesis of 2-(2-(phthalimido)ethoxy)ethyl-2-cyanoethyl-N,N-diisopropylphosphoramidite.

5.0 g phthalic anhydride were dispersed in 75 mL toluene and added 3.7 g 2-aminoethoxy-ethanol. The reaction mixture was heated to reflux under a Dean-Stark trap and a nitrogen atmosphere. After refluxing for 2.5 hr., the reaction mixture was cooled to the ambient temperature, and washed with 2×12 mL 1:1 brine-water and 12 mL brine. Drying (anhydrous MgSO$_4$), filtering, and stripping to give 6.51 g of a white solid of N-(2-hydroxyethoxy)ethyl-phthalimide. This solid was use without purification in the subsequent synthesis.

1 g N-(2-hydroxyethoxy)ethyl-phthalimide dissolved in 8 mL dichlormethane was stirred, and added dropwise sequentially 0.8 mL diisopropylethylamine and a solution prepared from 1 mL 2-cyanoethyl diisopropylchlorophosphoramidite and 2 mL dichloromethane. After stirring at the ambient temperature for about 1.5 hr., the reaction mixture was washed with 12 mL water and 12 mL brine, and concentrated. The concentrated residue was flashed through a silica gel column with 1:1 ethyl acetae-hexane. The desired fractions were combined, stripped, and dried under high vacuum to give 0.94 g of a clean oily product. $^1$H NMR(CDCl$_3$): 7.84 (dd, 2H), 7.71 (dd, 2H), 3.88 (t, 2H), 3.84–3.6 (m, 8H), 3.54 (m, 2H), 2.61 (m, 2H), 1.10 (dd, 12H).

Synthesis of 2-(2-(2-(phthalimido)ethoxy)ethoxy)ethyl-2-cyanoethyl-N,N-diisopropylphosphoramidite.

2.0 mL (11 mmol) dry 76%triethylene glycol in toluene, 1.9 g (13 mmol) phthalimide, and 3.5 g (13 mmol) triphenylphosphine were stirred in 20 mL dry THF at the ice-water temperature, and added 2.6 mL (13 mmol) diisopropyl azodicarbonate in about 5 min. After the addition was completed, the reaction mixture was stirred at the ambient temperature for about 12 h. 2 mL methanol was then added, and the reaction mixture was stirred for 10 min. The white solids were removed by filtration, and the filtrate was stripped to give a thick oily residue. The oily residue was added ether, filtered to remove the white solids of triphenylphosphine oxide, and stripped to give 5.3 g of a clean oil. 1.5 g of the oil were dissolved in 2 mL dicholormethane and extracted with 2×3 mL water. The combined water layers were stripped under high vacuum to give a clean oily residue. The oily residue was added 4 mL of 3:1 brine-water and extracted with 2×2 mL ethyl acetate. The combined ethyl acetate layers were dried over anhydrous MgSO$_4$, filtered, stripped, and dried under high vacuum to give 56 mg of an oily residue of crude N-(2-(2-(2-hydroxyethoxy)ethoxy)ethyl)phthalimide This residue was used directly without further purification in the subsequent synthesis.

56 mg (0.20 mmol) of the oily residue was dissolved in about 1.5 mL dichloromethane, stirred, and added sequentially 42 μL (0.24 mmol) diisopropylethylamine and 54 μL (0.24 mmol) 2-cyanoethyl diisopropyl chlorophosphoramide. After the addition was completed, the reaction mixture was stirred at the ambient temperature for about 40 min. A quarter of the reaction mixture was flashed through a short silica gel column, and the desired fractions were collected and combined. The combined fractions were stripped and dried under high vacuum to give 14 mg of an oily product. $^1$H NMR(CDCl$_3$): 7.84 (m, 2H), 7.71 (m, 2H), 3.90 (m, 2H), 3.8–3.6 (m, 14H), 2.64 (t, 2H), 1.26 (d, 6H), 1.26 (d, 6H).

Preparation of N-(2-hydroxyethyl)phthalimido Molecule Covalently Attached to CPG (Controlled Pore Glass) Beads.

1 g Beckman 1000 A Universal Beads (38.6 μmol/g), 0.4 g (2.0 mmol) trimellitic anhydride, 1 g (2.3 mmol) BOP, 12 mL dry DMF, and 1.0 mL (5.7 mmol) diisopropylethylamine were charged sequentially to a 20 mL reaction vial. The reaction vial was capped, and the reaction mixture was shaken on a shaker for about 4 hr. The beads were collected by filtration, followed by washing with 20 mL methanol and 20 mL acetone. After drying under high vacuum, the beads of phthalic anhydride terminated were used for the synthesis of the N-(2-hydroxyethyl)-phthalimido terminated linker on the same beads.

400 mg of these beads was added to 4 mL chloroform and 1 mL aminoethanol in a reaction vial. The reaction vial was then capped and heated at about 70° C. on a rotating heating block for about 22 h. The desired beads were recovered by filtration, repeatedly washing with dichloromethane, methanol, and dichloromethane, and drying under high vacuum. The titer value found by the titration method using 4,4'-dimethoxytrityl chloride is about 24 μmol/g.

Preparation of N-(2-(2-hydroxyethoxy)ethyl)phthalimido Molecule Covalently Attached to CPG Beads.

300 mg of the same beads with surface covalently formed phthalic anhydride molecule prepared in the above synthesis was added 3 mL chloroform and 1.2 mL 2-(2-aminoethoxy) ethanol in a reaction vial. The reaction vial was capped and heated at about 70° C. on a rotating heating block for about 16 h. The desired beads were recovered by filtration, repeatedly washing with dichloromethane, methanol, and dichloromethane, and drying under high vacuum. The titer value found by the titration method using 4,4'-dimethoxytrityl chloride is about 21 μmol/g.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed:

1. A compound of formula (I):

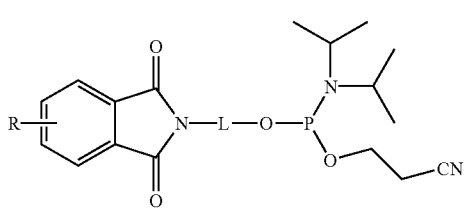

(I)

wherein

R is hydrogen, $C_{1-6}$ alkyl, $C_{1-6}$ alkoxyl, or a halogen; and

L is a bond, a nucleotide residue, a nucleotide oligomer, aryl, heteroaryl, $C_{1-14}$ cycloalkyl, $C_{1-12}$ heterocycloalkyl, S, NH, or $(R_1-(O)_m)_n-R_1$, in which $R_1$ is $C_{1-4}$ alkylene, $C_{1-4}$ alkenylene, or $C_{1-4}$ alkynylene, m is 1 or 0, and n is 1 to 12.

2. The compound of claim 1, wherein R is H, and L is $(R_1-(O)_m)_n-R_1$, in which $R_1$ is $C_{1-4}$ alkylene, $C_{1-4}$ alkenylene, or $C_{1-4}$ alkynylene.

3. The compound of claim 2, wherein $R_1$ is $CH_2CH_2$, m is 1, and n is 1–4.

4. The compound of claim 3, wherein n is 1 or 2.

5. The compound of claim 2, wherein $R_1$ is $CH_2CH_2$, m is 0, and n is 1–4.

6. A compound of formula (II):

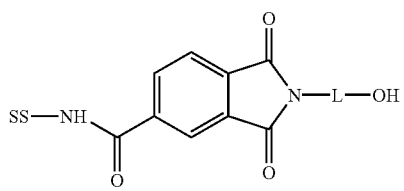

(II)

wherein L is a bond, a nucleotide residue, a nucleotide oligomer, aryl, heteroaryl, $C_{1-14}$ cycloalkyl, $C_{1-12}$ heterocycloalkyl, S, NH, or $(R_1-(O)_m)_n-R_1$, in which $R_1$ is a $C_{1-4}$ alkylene, $C_{1-4}$ alkenylene, or $C_{1-4}$ alkynylene, m is 1 or 0, n is 1 to 12, and SS is a solid support.

7. The compound of claim 6, wherein R is H, and L is $(R_1-(O)_m)_n-R_1$, in which $R_1$ is $C_{1-4}$ alkylene, $C_{1-4}$ alkenylene, or $C_{1-4}$ alkynylene.

8. The compound of claim 7, wherein m is 1.

9. The compound of claim 8, wherein $R_1$ is $CH_2CH_2$, and n is 1–4.

10. The compound of claim 9, wherein n is 1 or 2.

11. The compound of claim 7, wherein m is 0.

12. A compound of formula (III):

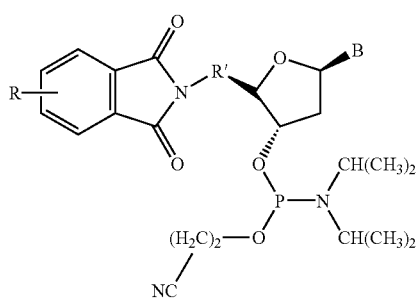

(III)

wherein R is hydrogen, $C_{1-6}$ alkyl, $C_{1-6}$ alkoxyl, or a halogen; R' is $C_{1-12}$ alkylene, $C_{1-12}$ alkenylene, or $C_{1-12}$ alkynylene; and B is a nucleotide base.

13. The compound of claim 12, wherein R is H and R' is $CH_2$.

14. The compound of claim 13, wherein B is a adenine, guanine, thymidine, uridine, or cytidine.

15. A method of preparing a polynucleotide, comprising:

coupling a first nucleotide or a first nucleotide oligomer to the terminal hydroxyl group of the compound of formula (II):

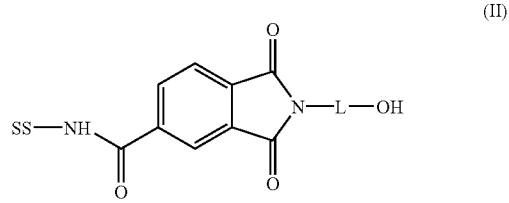

(II)

wherein L is a bond, aryl, heteroaryl, $C_{1-14}$ cycloalkyl, $C_{1-12}$ heterocycloalkyl, S, NH, or $(R_1-(O)_m)_n-R_1$, in which $R_1$ is a $C_{1-4}$ alkylene, $C_{1-4}$ alkenylene, or $C_{1-4}$ alkynylene, m is 1 or 0, n is 1 to 12, and SS is a first solid support, to obtain a compound of formula (IV)

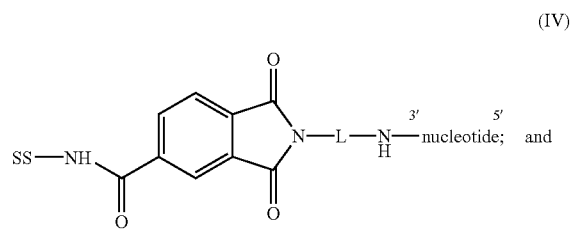

(IV)

treating the compound of formula (IV) with a strong base to release a nucleotide or polynucleotide having a 340 amino group.

16. The method of claim 15, wherein the strong base is ammonia.

17. The method of claim 15, wherein R is H, and L is $(R_1-(O)_m)_n-R_1$, in which $R_1$ is $C_{1-4}$ alkylene, $C_{1-4}$ alkenylene, or $C_{1-4}$ alkynylene, m is 1, and n is 1 to 7.

18. The method of claim 15, further comprising, before the treating, sequentially coupling additional nucleotides or additional nucleotide oligomers to the first nucleotide or the first nucleotide oligomer to form an extended polynucleotide attached to the support.

19. The method of claim 15, further comprising covalently bonding the amino group of the released nucleotide to a second support.

20. The method of claim 18, wherein monomeric nucleotides are coupled.

21. A method to preparing a 5'-amino labeled nucleotide, comprising:

sequentially coupling nucleotides to a solid support to obtain a precursor oligonucleotide;

coupling a compound of formula (I) or (III) to the precursor oligonucleotide

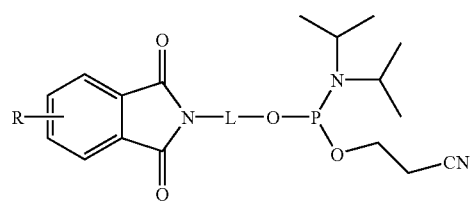

(I)

wherein R is hydrogen, $C_{1-6}$ alkyl, $C_{1-6}$ alkoxyl, or a halogen; and L is a bond, a nucleotide residue, aryl, heteroaryl, $C_{1-14}$ cycloalkyl, $C_{1-12}$ heterocycloalkyl, S, NH, or $(R_1-(O)_m)_n-R_1$, in which $R_1$ is $C_{1-4}$ alkylene, $C_{1-4}$ alkenylene, or $C_{1-4}$ alkynylene, m is 1 or 0, and n is 1 to 12,

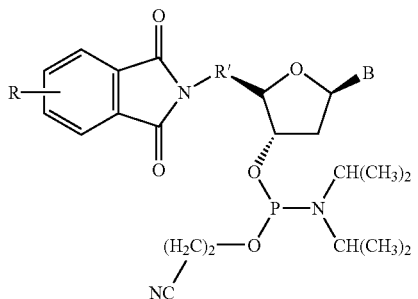

(III)

wherein R is hydrogen, $C_{1-6}$ alkyl, $C_{1-6}$ alkoxyl, or a halogen; R' is $C_{1-12}$ alkylene, $C_{1-12}$ alkenylene, or $C_{1-12}$ alkynylene; and B is a nucleotide base, to the 5' terminus of the precursor oligonucleotide thereby forming a 5'-modified oligonucleotide; and treating the 5'-modified oligonucleotide with a strong base to release the terminated oligonucleotide and a modifying group to form a 5' amino labeled oligonucleotide.

22. The method of claim 21, further comprising coupling the 5' amino labeled oligonucleotide to a substrate.

23. The method of claim 22, wherein the strong base is ammonia.

* * * * *